(12) United States Patent
Yagi et al.

(10) Patent No.: US 7,306,657 B2
(45) Date of Patent: Dec. 11, 2007

(54) OXYGEN CONCENTRATING APPARATUS

(75) Inventors: Hideaki Yagi, Aichi (JP); Junichi Akiyama, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 428 days.

(21) Appl. No.: 10/973,286

(22) Filed: Oct. 27, 2004

(65) Prior Publication Data

US 2005/0139214 A1   Jun. 30, 2005

(30) Foreign Application Priority Data

Oct. 28, 2003   (JP)   ............................ 2003-366769
Oct. 26, 2004   (JP)   ............................ 2004-311045

(51) Int. Cl.
*B01D 53/02*   (2006.01)
(52) U.S. Cl. .............. 96/121; 128/204.23; 128/204.26; 128/205.12; 128/205.24; 128/205.27
(58) Field of Classification Search .................... 95/96; 128/205.12, 205.27, 204.23, 204.26, 205.24; 96/121, 130, 133
See application file for complete search history.

(56) References Cited

U.S. PATENT DOCUMENTS 4,932,402 A * 6/1990 Snook et al. .......... 128/204.23

6,446,630 B1 * 9/2002 Todd, Jr. ............... 128/204.18
2002/0040714 A1   4/2002 Yagi et al.

FOREIGN PATENT DOCUMENTS

| JP | 2000-79164 | A | 3/2000 |
| JP | 2000-300673 | A | 10/2000 |
| JP | 2001-129086 | A | 5/2001 |
| JP | 2001-163605 | A | 6/2001 |
| JP | 2002-85566 | A | 3/2002 |
| JP | 3288903 | B2 | 3/2002 |
| JP | 2002-253675 | A | 9/2002 |
| JP | 2002-253676 | A | 9/2002 |
| JP | 2003-126261 | A | 5/2003 |
| JP | 2003-146621 | A | 5/2003 |
| JP | 2003-180837 | A | 7/2003 |
| JP | 2003-275313 | A | 9/2003 |
| JP | 2003-286009 | A | 10/2003 |

* cited by examiner

*Primary Examiner*—Robert A. Hopkins
(74) *Attorney, Agent, or Firm*—Sughrue Mion, PLLC

(57) ABSTRACT

An oxygen concentrating apparatus including an output variable type compressor. Oxygen-concentrated gas may be supplied either continuously or synchronized with inhalation or timing of inhalations. In one aspect, when synchronous operation is selected, the compressor is operated at a lower output in comparison with continuous supply operation. In a second aspect, when synchronous operation is selected, the supply quantity of oxygen-concentration gas is set to zero during the exhalation period.

16 Claims, 8 Drawing Sheets

OXYGEN CONCENTRATING APPARATUS

BACKGROUND OF THE INVENTION

1. Field of the Invention

The present invention relates to an oxygen concentrating apparatus for supplying an oxygen-concentrated gas of high oxygen concentration to an inhaler.

2. Description of the Related Art

An example of a conventional oxygen concentrating apparatus, is described in JP-A-2002-85566 Gazette (Patent Document 1) of the present inventors. The oxygen concentrating apparatus described therein has a compressor for taking in and supplying compressed air, a concentration means for increasing the oxygen concentration of the compressed air to thereby obtain an oxygen-concentrated gas, a gas tank for storing the oxygen-concentrated gas obtained from the concentration means, a gas outlet for supplying the oxygen-concentrated gas stored in the gas tank to an inhaling person, a respiration detection means for distinguishing the respiration state of the inhaling person, a continuous supply control means for continuously discharging the oxygen-concentrated gas from the gas outlet, and a synchronous supply control means for supplying a set quantity of the oxygen-concentrated gas to the gas outlet synchronized with inhalation of the inhaling person. On the other hand, the synchronous supply control means reduces, during exhalation time, the supply quantity of oxygen-concentrated gas to the gas outlet and stores, during that time, the oxygen-concentrated gas in a gas tank to thereby prepare for the next inhalation. The apparatus is adapted so that, in response to a supply setting within a range of oxygen-concentrated gas that can continuously be supplied by the compressor and concentration means, the continuous supply control means is adjusted correspondingly. Furthermore, in response to a supply setting exceeding the range of oxygen-concentrated gas that can be continuously supplied by the compressor and the concentration means, the synchronous supply control means is adjusted correspondingly. When respiration synchronous operation by the synchronous supply control means is in effect, a surplus quantity of the oxygen-concentrated gas produced during the exhalation period is stored in the gas tank and, during inhalation the stored quantity is added to the gas that is supplied. Consequently, it is possible to meet the demands of a supply setting exceeding the range of gas that can be continuously supplied.

Because the oxygen concentrating apparatus mentioned above is set so that, in response to a supply setting within the range of oxygen-concentrated gas that can be continuously supplied, the continuous supply control means fixes the output of the compressor to a constant value, and in response to a supply setting exceeding the range of oxygen-concentrated gas that can be continuously supplied the synchronous supply control means is adjusted, a problem arises in that a constant amount of electric power is consumed irrespective of the quantity of the oxygen-concentrated gas that is required and thus the electricity burden cost is large.

SUMMARY OF THE INVENTION

It is therefore an object of the present invention to provide an oxygen concentrating apparatus which conserves electric power. The above object has been achieved by providing:

(1) An oxygen concentrating apparatus comprising an output variable type compressor for taking in and supplying compressed air, a concentration means for increasing oxygen concentration of air supplied by the compressor to thereby produce an oxygen-concentrated gas, a gas tank for storing the oxygen-concentrated gas produced by the concentration means, a gas outlet for supplying oxygen-concentrated gas stored in the gas tank to an inhaling person, a respiration detection means for distinguishing a respiration stage of the inhaling person, a continuous supply control means for continuously discharging oxygen-concentrated gas from the gas outlet, a synchronous supply control means for supplying oxygen-concentrated gas to the gas outlet, said supply being synchronized with inhalation or timing of inhalations of the inhaling person, and for storing oxygen-concentrated gas in the gas tank when it is not being supplied to the inhaling person, and a continuous/synchronous change-over means for allowing a user to select one of the continuous supply control means and the synchronous supply control means for supplying said oxygen-concentrated gas within a range that can be continuously supplied by the compressor and the concentration means.

As used herein, an "inhaling person" is a person who inhales the oxygen-concentrated gas, and may be, for example, a patient who has a respiratory disease, a healthy person who desires high concentration oxygen, and the like. Further, the "user" is a person who operates the apparatus, and may be, for example, the inhaling person, a doctor, a nurse or the like, who operates the apparatus.

(2) In a preferred embodiment, the present invention provides an oxygen concentrating apparatus as described in (1) above, wherein the compressor, when synchronous supply control has been selected, is operated at a lower output in comparison with continuous supply operation in the case where the oxygen-concentrated gas supply quantity is set to the same level during both synchronous and continuous supply.

(3) In yet another embodiment, the present invention provides an oxygen concentrating apparatus as described in (1) or (2) above, wherein the respiration detection means distinguishes the respiration stage of the inhaling person by movement of gas in the gas outlet.

(4) In yet another embodiment, the present invention provides an oxygen concentrating apparatus as described in any one of (1) to (3) above, wherein when respiration synchronous operation is selected, said synchronous supply control means reduces the supply quantity of the oxygen-concentrated gas to the gas outlet at times other than when the oxygen-concentrated gas is being supplied to the gas outlet, said supply being synchronized with inhalation or timing of inhalations of the inhaling person.

(5) In yet another embodiment, the present invention provides an oxygen concentrating apparatus as described in any one of (1) to (3) above, wherein when respiration synchronous operation is selected, said synchronous supply control means sets the supply quantity of oxygen-concentrated gas to the gas outlet to zero at times other than when the oxygen-concentrated gas is being supplied to the gas outlet, said supply being synchronized with inhalation or timing of inhalations of the inhaling person.

(6) Preferably when respiration synchronous operation is selected, the supply of oxygen-concentrated gas of the gas outlet is synchronized with the entire inhalation or timing of inhalations of the inhaling person.

In a respiration synchronous operation by the synchronous supply control means, because the quantity of oxygen-concentrated gas blown out from a nose cannula is remarkably reduced during exhalation, drying of the mucosa of the nose or throat can advantageously be reduced. On the other hand, continuous supply operation by the continuous supply control means provides a safe feeling that oxygen-concentrated gas is always being supplied. Because the user can select either respiration synchronous operation or continuous supply operation, it is possible to suitably adapt to the individual needs of the inhaling person according to his/her physical condition and psychological state while conserving electricity, so that ease of use is remarkably improved.

Further, consider a case where the user has selected synchronous supply via the continuous/synchronous change-over means for operation within the range of oxygen-concentrated gas that can be continuously supplied by the compressor and the concentration means. If the output variable compressor is operated at a lower output in comparison with continuous supply operation in the case where the oxygen-concentrated gas supply quantity has been set to the same level as for continuous supply, the electric power used in a case of oxygen-concentrated gas supply at the lower flow rate is less than that of the prior art. In order to control the compressor in this manner, it is desirable to previously set the compressor as in (2) above.

Further, as in (3) above, if the respiration detection means is adapted so that the respiration state of the inhaling person is distinguished by movement of gas in the gas outlet, it is possible to flexibly adapt to both single and double type nose cannula described below.

Further, in the oxygen concentrating apparatus of (4) above, when respiration synchronous operation is selected, the synchronous supply control means reduces the supply quantity of the oxygen-concentrated gas to the gas outlet at times other than when oxygen-concentrated gas is supplied to the gas outlet, the supply being synchronized with inhalation or the timing of inhalations of the inhaling person. Namely, a small quantity of steady flow is supplied during the exhalation period, and it is possible to enjoy both the advantages of saving electricity, which is a characteristic of respiration synchronous operation, and a psychological safety feeling which is characteristic of the continuous supply operation Further, since the oxygen concentrating apparatus of (5) above can reduce electricity consumption of the concentration means for the oxygen-concentrated gas when the supply quantity of the oxygen-concentrated gas to the gas outlet is zero at times other than when the oxygen-concentrated gas is being supplied to the gas outlet while the supply of oxygen-concentrated gas is synchronized with inhalation or the timing of inhalations of the inhaling person, i.e., approximately during the exhalation period, the electric power savings effect becomes most apparent.

DETAILED DESCRIPTION OF THE INVENTION

Figure 1:
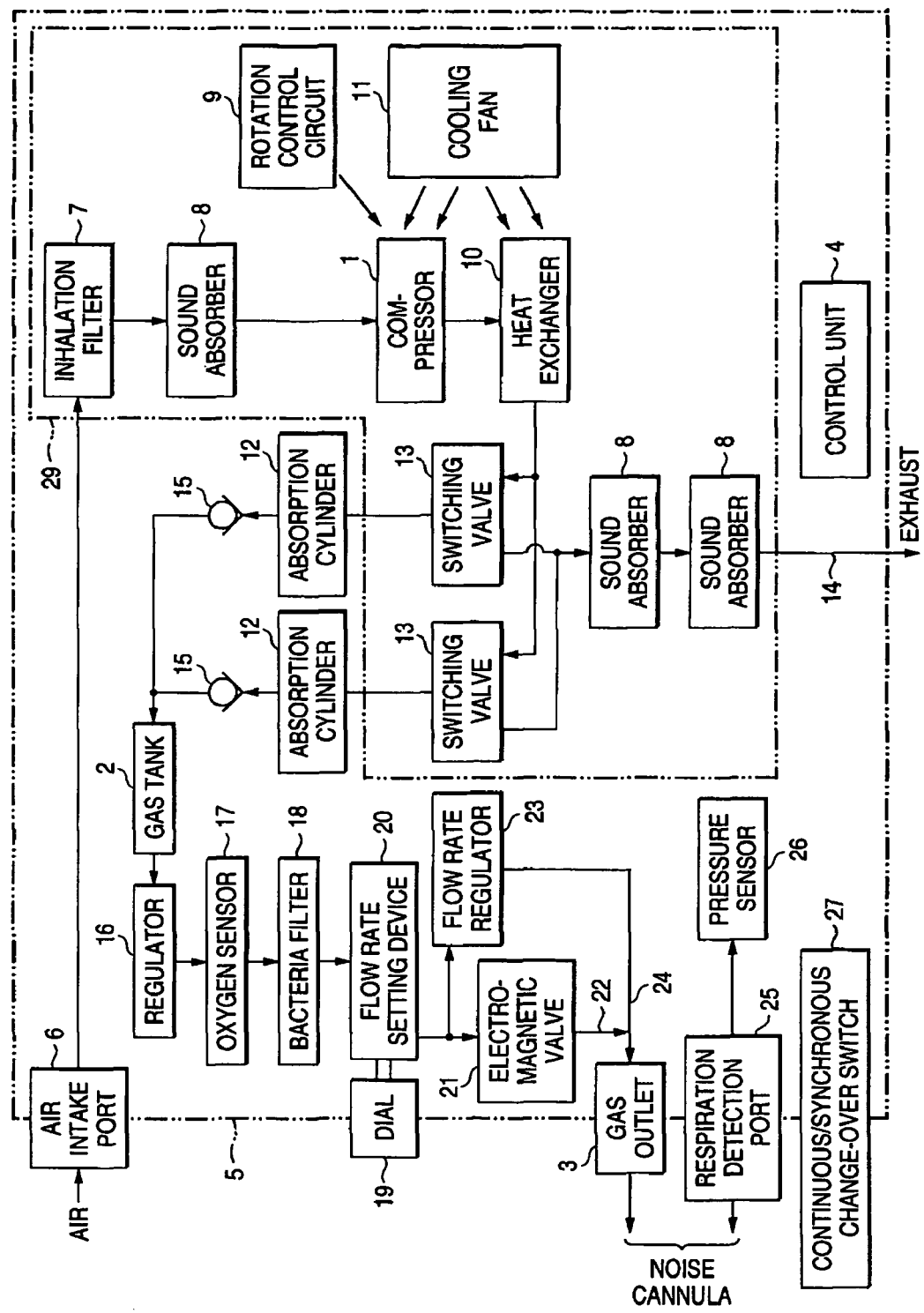
FIG. 1 is a block diagram showing operation of an oxygen concentrating apparatus of a first embodiment of the invention in outline form.

Next, an embodiment of the present invention is explained in reference to the drawings. However, the present invention should not be construed as being limited thereto As shown in FIG. 1, an oxygen concentrating apparatus generally comprises a compressor 1 for taking in and supplying compressed air, a concentration means for increasing oxygen concentration of air supplied by the compressor 1 to thereby produce an oxygen-concentrated gas (hereafter, also referred to as "oxygen"), a gas tank 2 for storing oxygen produced by the concentration means, a gas outlet 3 for supplying oxygen stored in the gas tank 2 to an inhaling person, a respiration detection means for distinguishing the respiration stage of the inhaling person, a continuous supply control means for continuously discharging oxygen from the gas outlet 3, a synchronous supply control means for supplying oxygen to the gas outlet 3 synchronized with inhalation or timing of inhalations, and for reducing a supply quantity of oxygen to the gas outlet 3 at other times during which oxygen is being stored in the gas tank 2, and a control unit 4 for controlling the above constituent elements accommodated in a single case body 5.

The compressor 1 is connected to an air intake port 6 of the case body 5 through an inhalation filter 7 and a sound absorber 8, and takes in the outside air from air intake port 6 and pressurizes and then supplies it to the concentration means. The compressor 1 is a compressor of an output variable type, e.g., an inverter type, and its output can optionally be changed via control by a rotation control circuit 9 constituting a part of the control unit 4.

A heat exchanger 10 is connected to an air supplying side of the compressor 1. Further, a cooling fan 11 is installed near compressor 1 and heat exchanger 10, and compressor 1 is cooled by the cooling fan 11. Further, oxygen whose temperature has been raised by compression is cooled by the cooling fan 11 and the heat exchanger 10.

Further, a sound absorbing case 29 accommodates the inhalation filter 7, the sound absorber 8, the compressor 1, the heat exchanger 10, the rotation control circuit 9, the cooling fan 11, and switching valves 13, 13 described below.

The concentration means described above increases oxygen concentration of the air supplied by compressor 1, and is constituted by a pair of adsorption cylinders 12, 12 filled with a zeolite-based adsorbent, for example, and one pair of switching valves 13, 13 which alternately switch the adsorption cylinders 12, 12 connected to the compressor 1. The zeolite-based adsorbent filled in the adsorption cylinders 12, 12 when pressurized to about 140 kPa preferentially adsorbs nitrogen in the air to thereby increase oxygen concentration. When depressurized to atmospheric pressure, the adsorbent discharges the previously adsorbed nitrogen to thereby return to its original state. A high oxygen concentration is obtained when compressed air is supplied to one adsorption cylinder 12 from the compressor 1, while nitrogen is discharged from the other adsorption cylinder 12 when it is depressurized by connecting to an exhaust flow passage 14, to thereby regenerate the adsorbent.

The concentration means suffices if it delivers an oxygen concentration suitable for the intended use, and may utilize means other than the above, such as an oxygen selection transmission film (oxygen enrichment film).

The gas tank 2 is pipe-connected to the pair of adsorption cylinders 12, 12 through check valves 15, 15, and stores the oxygen made by the concentration means and discharges the stored oxygen toward the gas outlet 3.

Figure 4:
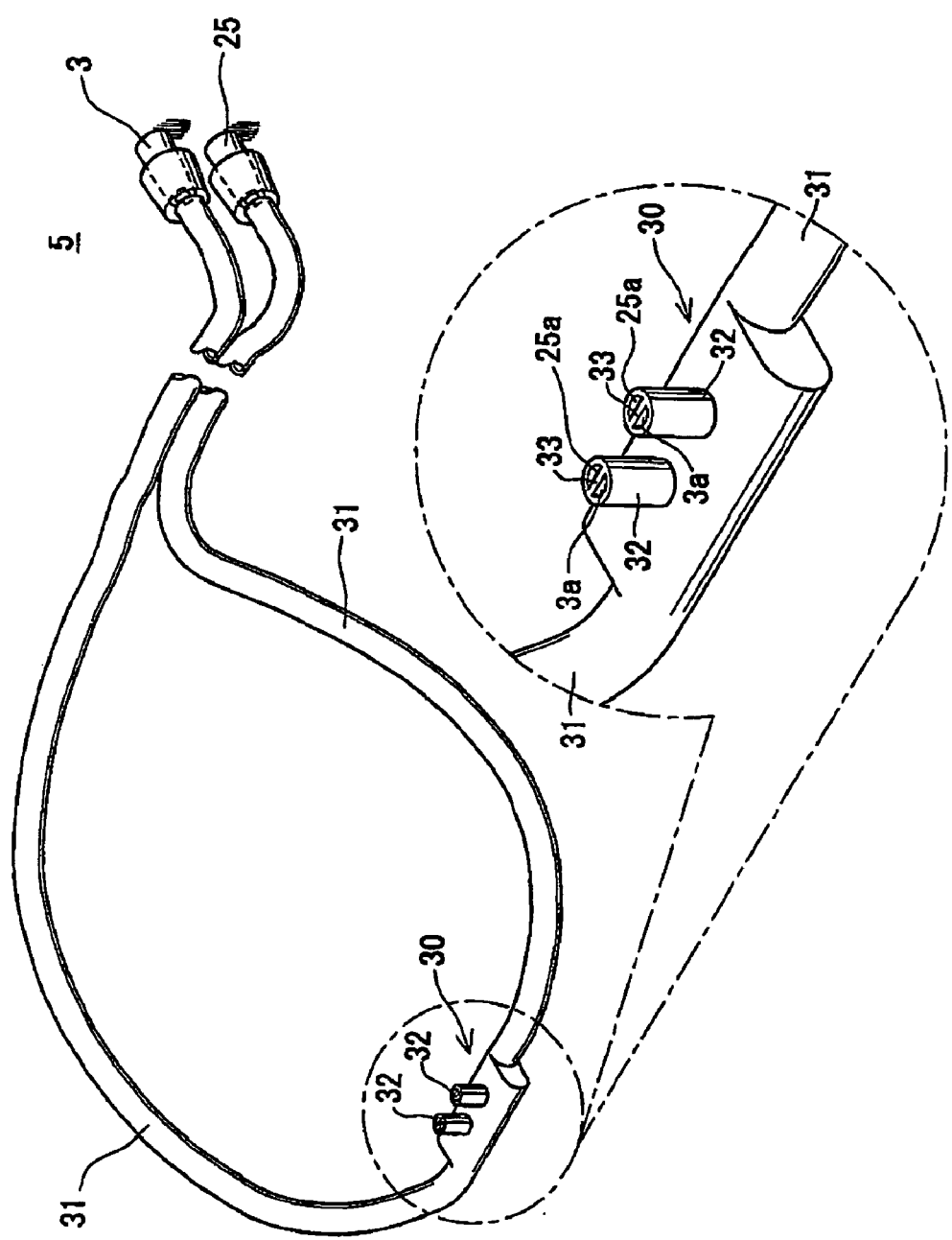
FIG. 4 is a perspective view showing a nose cannula.

The gas outlet 3 supplies the oxygen stored in the gas tank 2 to the inhaling person and, as shown in FIG. 4, a tube 31 communicating with nose cannula 30 is connected to the gas outlet 3. Nose cannula 30 is a pipe supplying oxygen to the nares of an inhaling person, and is conventionally known as an open type oxygen supply means. The nose cannula 30 shown in FIG. 4 is a double type cannula, and one of two tubes 31, 31 is connected to the gas outlet 3 and the other tube 31 is connected to a respiration detection port 25 described below. Accordingly, in each of short pipes 32, 32 applied to the nares, a partition 33 (refer to enlarged view of FIG. 4) is provided in its center in order to divide the flow passage of each of the tubes 31, 31. Further, in the enlarged view of FIG. 4, one of the pipe passages 25a of the short pipe 32 defined by the partition 33 communicates with the respiration detection port 25, and the other pipe passage 3a communicates with the gas outlet 3.

Between the gas outlet 3 and the gas tank 2 are provided a regulator 16 for reducing the pressure of oxygen delivered from the gas tank 2 to a suitable level, an oxygen sensor 17 for detecting the oxygen concentration, a bacteria filter 18 for preventing passage of bacteria, a flow rate setting device 20 which sets a flow rate of the oxygen by a rotary dial 19 attached to a user's operation panel (not shown in the drawing) in a front face of the case body 5, a main flow passage 22 provided with an open/close function by an electromagnetic valve 21, and a sub-flow passage 24 which has a flow rate regulator 23 and bypasses the electromagnetic valve 21. The flow rate regulator 23 of the sub-flow passage 24 sets an upper limit of the quantity of oxygen flowing through the sub-flow passage 24.

The respiration detection means described above distinguishes the respiration stage of the inhaling person by a pressure sensor 26 provided in the respiration detection port 25, and distinguishes inhalation and exhalation by first detecting the pressure on inhalation through the nose cannula 30. The respiration detection means is not limited to a structure based on pressure sensor 26, and may be adapted so that, e.g., a temperature difference between exhalation and inhalation is detected by a temperature sensor.

The continuous supply control means and the synchronous supply control means described above are connected to and controlled by control unit 4.

That is, the continuous supply control means has, as its main constituent elements, the flow rate setting device 20, the electromagnetic valve 21, the flow rate regulator 23 and the compressor 1 and, if the user inputs a supply setting for the oxygen by the dial 19, the flow rate of the flow rate setting device 20 is set to that value. Further, the control unit 4 controls output of the compressor 1 through the rotation control circuit 9 so that oxygen of the above supply setting is supplied to the gas outlet 3, and additionally opens the main flow passage 22 and the sub-flow passage 24 by opening the electromagnetic valve 21, thereby ensuring a necessary and sufficient flow passage communicating with the gas outlet 3. Accordingly, in a state under which the continuous supply control means is operating, oxygen in accordance with the supply setting inputted by the user is continuously supplied from the gas outlet 3.

On the other hand, the synchronous supply control means has, as its main constituent elements, the respiration detection means, the flow rate setting device 20, the electromagnetic valve 21, the flow rate regulator 23 and the compressor 1. As shown in a graph of a respiration cycle of FIG. 6, when the user inputs an oxygen supply setting by the dial 19, the flow rate of the flow rate setting device 20 is set to that value. Further, the control unit 4 controls, on the basis of the above supply setting, the output (explained in greater detail below) of the compressor 1 to a value lower than the supply setting in accordance with a program that was previously inputted. Based on an output of the respiration detection means, the electromagnetic valve 21 is opened so that the supply of oxygen is synchronized or coincident with the entire period of inhalation or with timing of the inhalations (for example, a case in which only the initial time of an inhalation is detected and a predetermined time period (5 seconds for instance) from that time is inferred to be the inhalation period) of the inhaling person, and oxygen at a flow rate satisfying the supply setting is supplied to the gas outlet 3 via the main flow passage 22 and the sub-flow passage 24. Further, at times other than the above, i.e., close to the exhalation time, the electromagnetic valve 21 is closed to thereby interrupt the main flow passage 22, and the supply quantity of oxygen to the gas outlet 3 is reduced to a flow rate prescribed by the flow rate regulator 23 of the sub-flow passage 23. The output of the compressor 1 is maintained unchanged even while the electromagnetic valve 21 is closed, and a temporary production surplus quantity (black mesh portion in FIG. 6) at exhalation is stored in the gas tank 2. By discharging oxygen from the gas tank 2 at the next inhalation time and adding such quantity to the output, the difference (in FIG. 6, this is shown by a slant line portion surrounded by a broken line and an alternate long and short dash line) between the output of the compressor 1 and the supply setting is made up.

The output of the compressor 1 during respiration synchronous operation of the synchronous supply control means is determined as follows.

Figure 6:
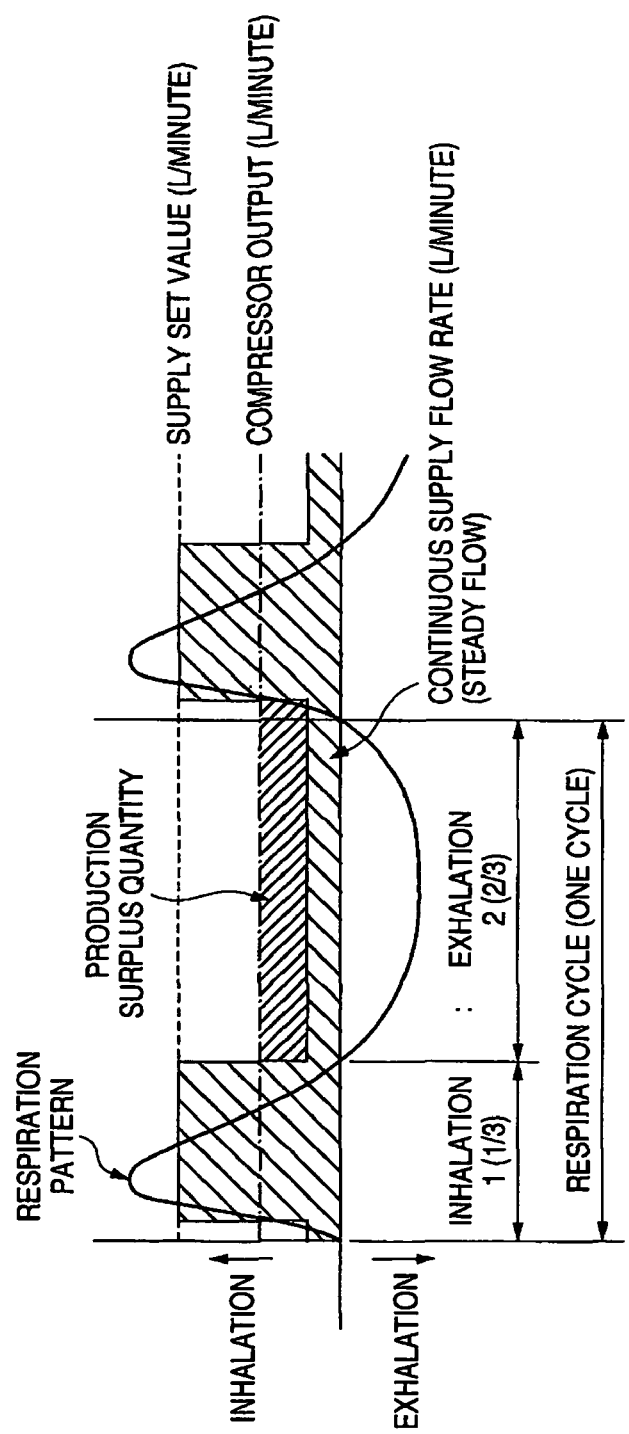
FIG. 6 is a graph superposing a gas supply pattern for respiration synchronous operation on a respiration cycle, including a level of steady flow during the exhalation period.

First, as seen in the respiration cycle shown in FIG. 6, the ratio of the inhalation time to the exhalation time of human respiration is about 1:2. Accordingly, the output (supply quantity) of the compressor 1 in respiration synchronous operation where the flow of oxygen is completely stopped during exhalation, such that the oxygen produced during that cycle is stored in the gas tank 2, is ⅓ that of a continuous supply operation whose oxygen supply setting is set to the same level as in synchronous operation. In other words, in a continuous supply operation, ⅔ of the manufactured oxygen is discarded during exhalation.

However, in a case where, during exhalation, oxygen at a low flow rate is continuously supplied as a steady flow, it suffices if, in view of the quantity of that steady flow, the output (supply quantity) of the compressor 1 is made about ½ of the oxygen produced in the continuous supply operation. In a case where the steady flow is increased, accurate control becomes possible by determining the output of the compressor 1 based on the formula ((supply setting−steady flow)/3+steady flow) and it is sufficient if the actual value is somewhat higher.

In the present invention, so that the user can select between continuous supply and synchronous supply (within a range of the oxygen-concentrated gas prepared by the compressor and the concentration means that can be continuously supplied), the operation panel described before is provided with a continuous/synchronous change-over switch 27. Accordingly, the user can select either continuous supply operation or respiration synchronous operation in view of conserving power consumption and the physical condition and psychological state of the inhaling person.

Although the present invention has been explained using the above embodiment, the present invention should not be construed as being limited thereto. For example, although the block diagram of FIG. 1 relates to the oxygen concentrating apparatus set so as to supply a steady flow during exhalation, in an oxygen concentrating apparatus in which the steady flow, i.e., the supply quantity of the oxygen to the gas exit 3, during exhalation is made zero, the invention can be achieved by removing the sub-flow passage 24 in FIG. 1 and restricting the supply of the oxygen to the main flow passage 22 alone.

Figure 2:
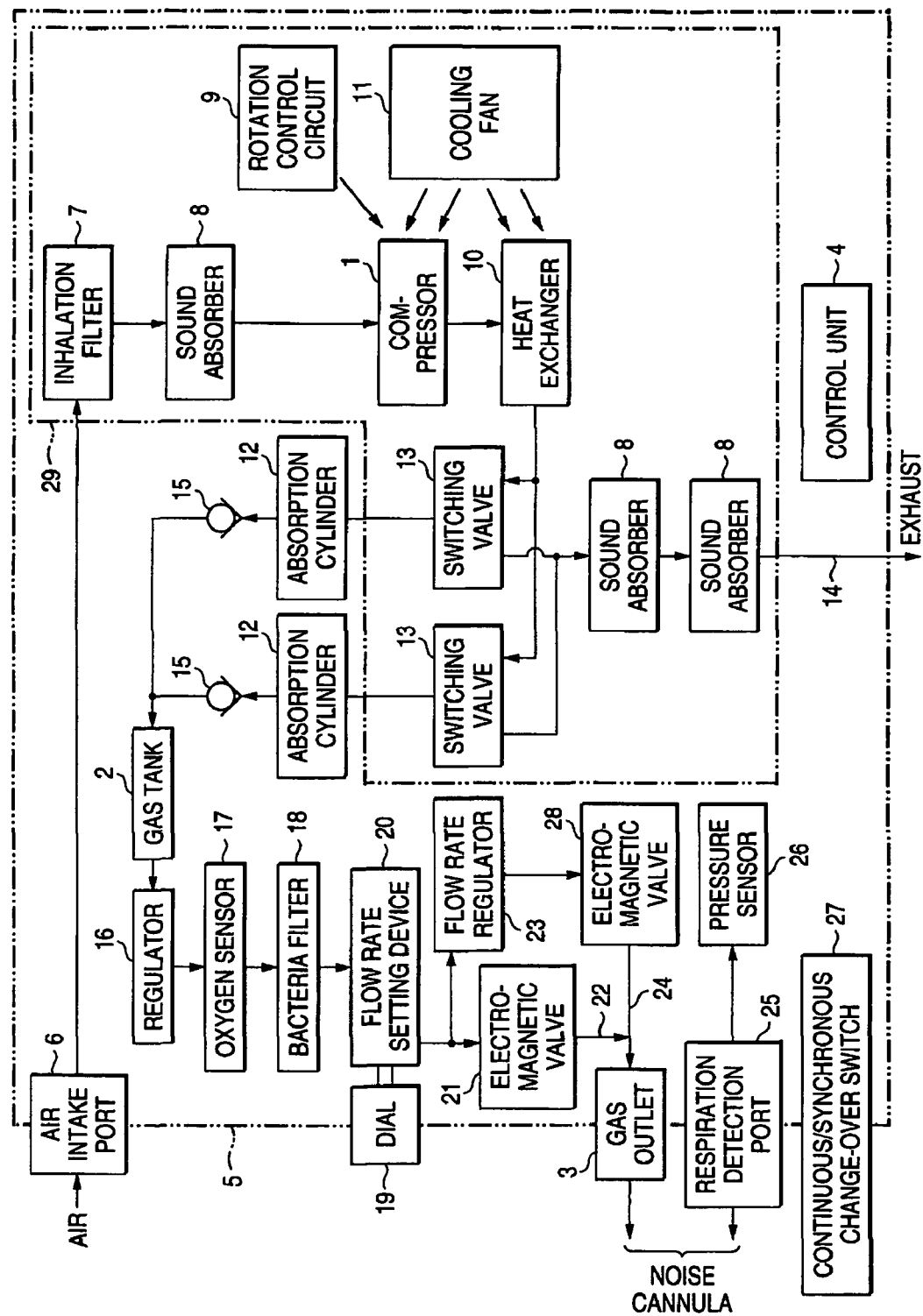
FIG. 2 is a block diagram showing operation of the oxygen concentrating apparatus of a second embodiment of the invention in outline form.

On the other hand, there is also a need to maintain a steady flow while the inhaling person is asleep in order to ensure safety, but the steady flow rate is reduced from the steady flow rate during daytime in order to preferentially achieve an energy savings. To meet such a demand, an electromagnetic valve 28 is added in the sub-flow passage 24 as shown in FIG. 2 and a selection switch (not shown in the drawing) by which the user selects whether a steady flow during respiration synchronous operation is additionally provided. Further, in the selection of whether or not steady flow is necessary, a control sub-program such as a "sleeping mode" for instance may be provided and an operation in which a steady flow mode is available but is automatically implemented only at sleeping time may be implemented. Alternatively, a steady flow may be automatically supplied if an abnormality (for example, when inhalation cannot be detected for a certain time, and the like) of respiration during sleeping time is detected. As a means for turning steady flow on or off, besides the above magnetic valve 28, an electromagnetic valve flow open/close function responding to mass flow for instance may be installed in the flow rate regulator 23 itself, or a valve (not shown in the drawing) for manually opening/closing the sub-flow passage 24 may be provided.

Figure 3:
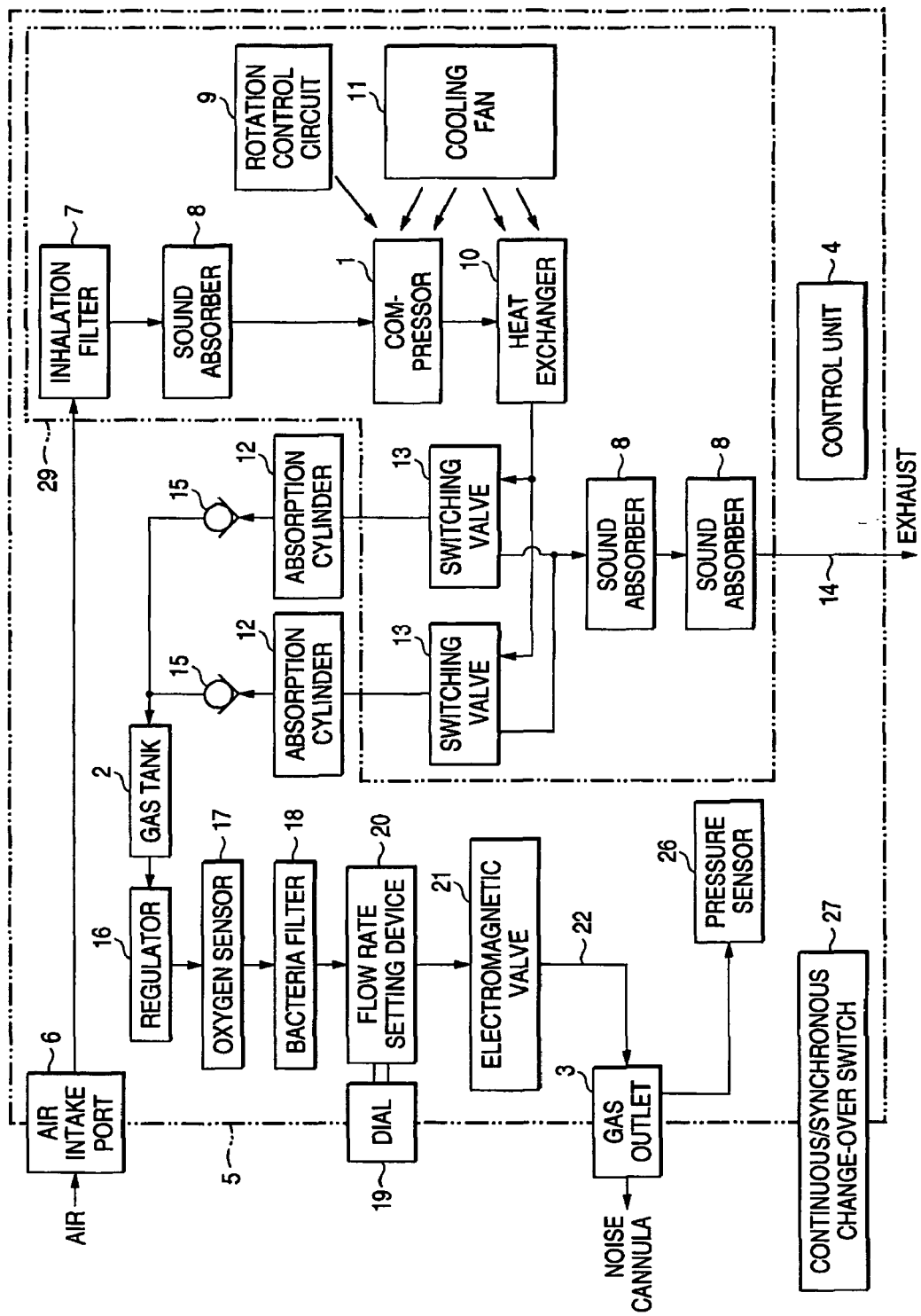
FIG. 3 is a block diagram showing operation of the oxygen concentrating apparatus of a third embodiment of the invention in outline form.
Figure 5:
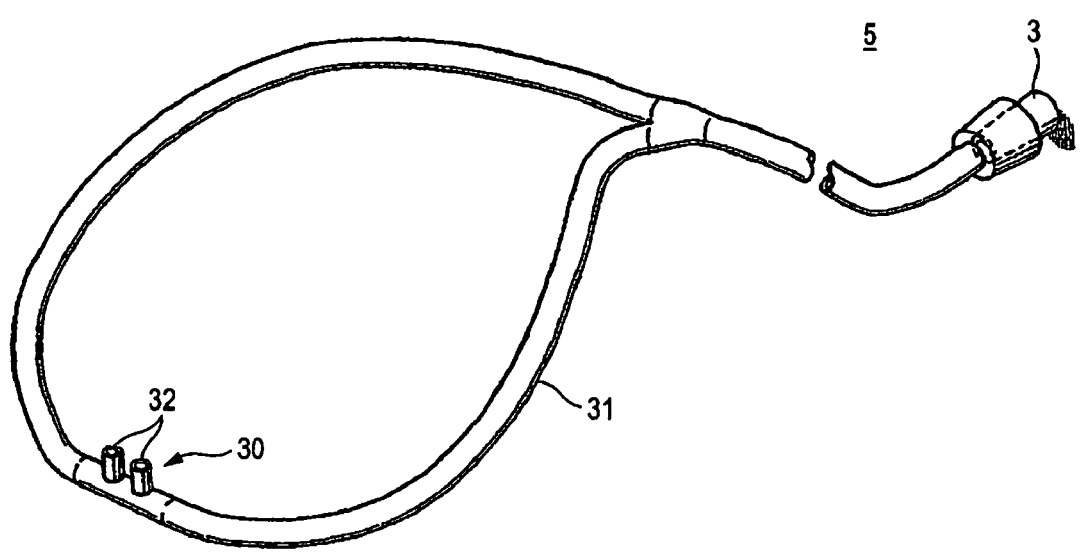
FIG. 5 is another perspective view showing the nose cannula.

Further, in the embodiment, although an independent respiration detection port 25 is provided and the pressure sensor 26 is provided therein to form the double type nose cannula 30, the pressure sensor 26 may be provided in the gas outlet 3 as shown in the block diagram of FIG. 3 when using a single type nose cannula 30 as shown in FIG. 5. The single type nose cannula 30 is one in which the two tubes 31, 31 are combined into one and connected to the gas outlet 3, and the respiration state of the inhaling person can be determined by the pressure sensor 26 provided in the gas outlet 3. If the embodiment is adapted to determine the respiration state of the inhaling person through the gas outlet 3, a single type nose cannula 30 can be used which is inexpensive and whose operability is good. In this case, the output indication of the compressor 1 generates oxygen in an amount of ⅓ that of the flow rate of the flow rate setting device 20 set by the dial 19, so that electricity consumption is remarkably reduced.

Figure 7:
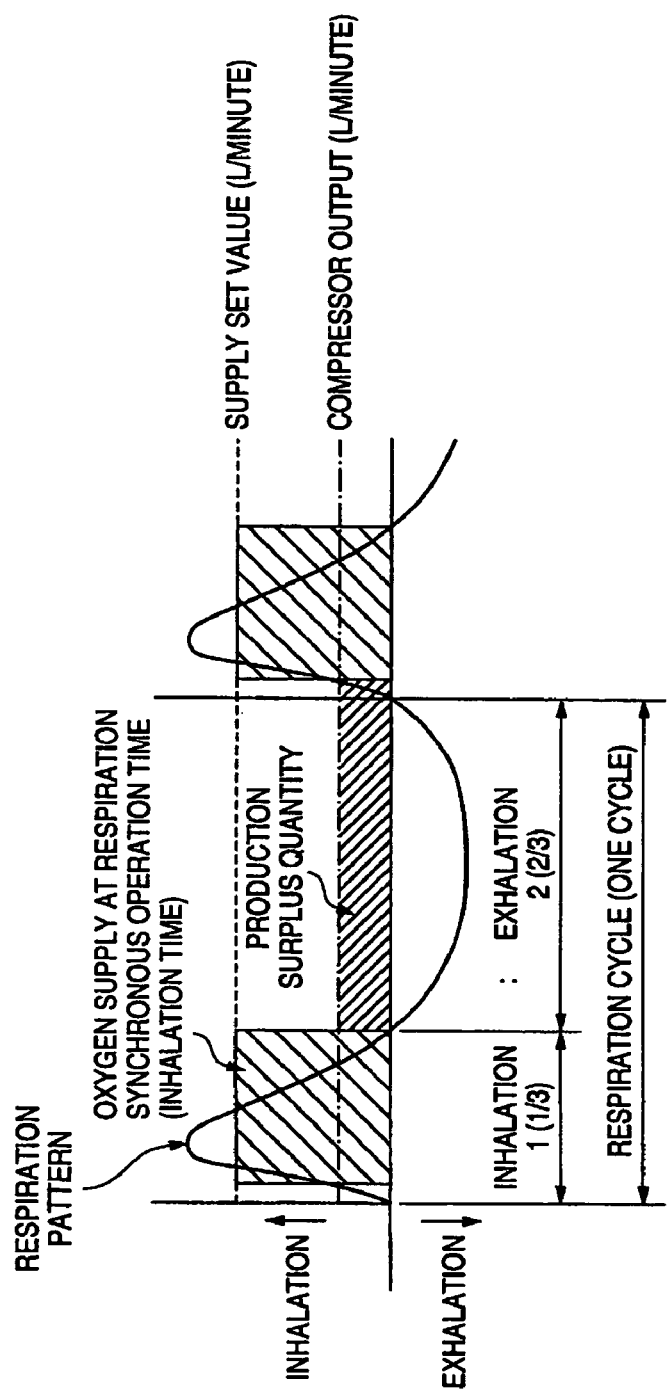
FIG. 7 is a graph superposing a gas supply pattern for respiration synchronous operation on a respiration cycle, where there is no steady flow during the exhalation period.

FIG. 7 shows a graph of a respiration cycle, on which a gas supply pattern during the respiration synchronous operation is superposed, in a first case where the steady flow during exhalation has been made null by removing the sub-flow passage 24 of FIG. 1, a second case where steady flow during exhalation has been made null in the oxygen concentrating apparatus of FIG. 3 and a case where the steady flow during exhalation has been set to OFF in the oxygen concentrating apparatus of FIG. 2. In these cases, since it is unnecessary to ensure a steady flow, the compressor 1 may be set to generate oxygen in an amount of ⅓ of the set flow rate, so that a more remarkable economization in electric power consumption becomes possible.

EXAMPLE 1

An oxygen supply apparatus was manufactured having a maximum oxygen supply rate of 5 L/minute. An inverter type compressor 1 was used having a maximum output of 3 L/minute, and the capacity of the concentration means was set so as to somewhat exceed 3 L/minute. The dial 19 inputting the supply setting was made so as to be capable of setting the rate to eleven levels "0.5, 0.75, 1.00, 1.25, 1.50, 2.00, 2.50, 3.00, 3.50, 4.00, 5.00". The apparatus was constituted such that the continuous supply control means was automatically operated in a case where the supply setting was lower than 1.0 L/minute. Further, either the continuous supply control means or the synchronous supply control means could be selected by the continuous/synchronous change-over switch 27 in a case where the supply setting was 1.25 L/minute-3.00 L/minute. Additionally, the synchronous supply control means was automatically operated in a case where the supply setting was higher than 3.50 L/minute. Further, a model was manufactured in which there was no steady flow, and another model in which a steady flow of 1 L/minute was supplied in a case where the supply setting was higher than 1.25 L/minute. Additionally, for comparison, a conventional type oxygen concentrating apparatus of the same class was prepared, which possessed no respiration synchronous function and in which the output of the compressor was constant as well.

Figure 8A:
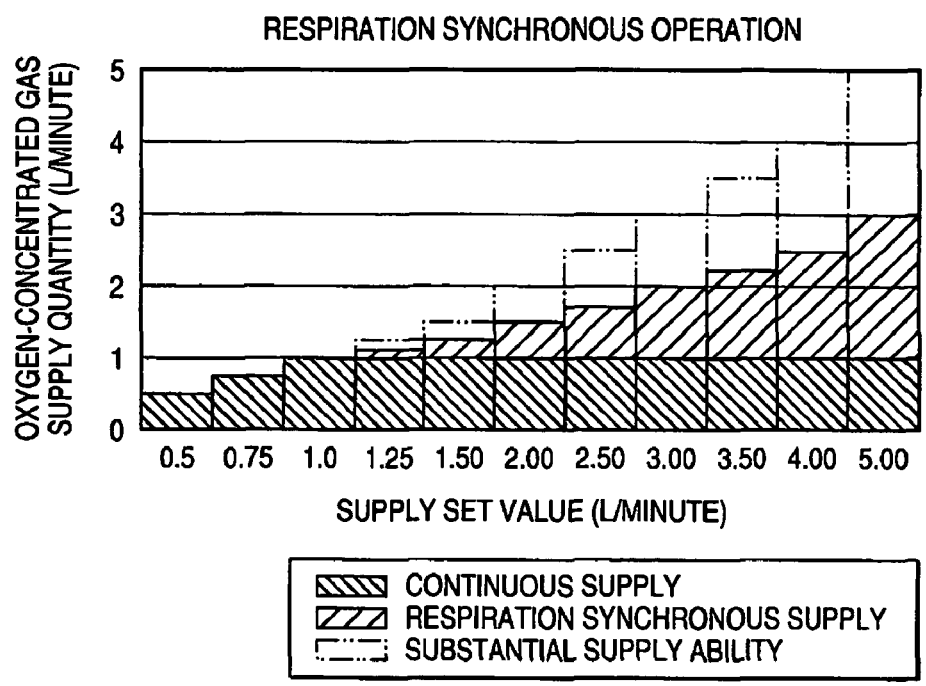
FIG. 8A is a graph showing the relationship between the set supply rate where respiration synchronous operation has been selected and the oxygen-concentrated gas supply quantity per minute.
Figure 8B:
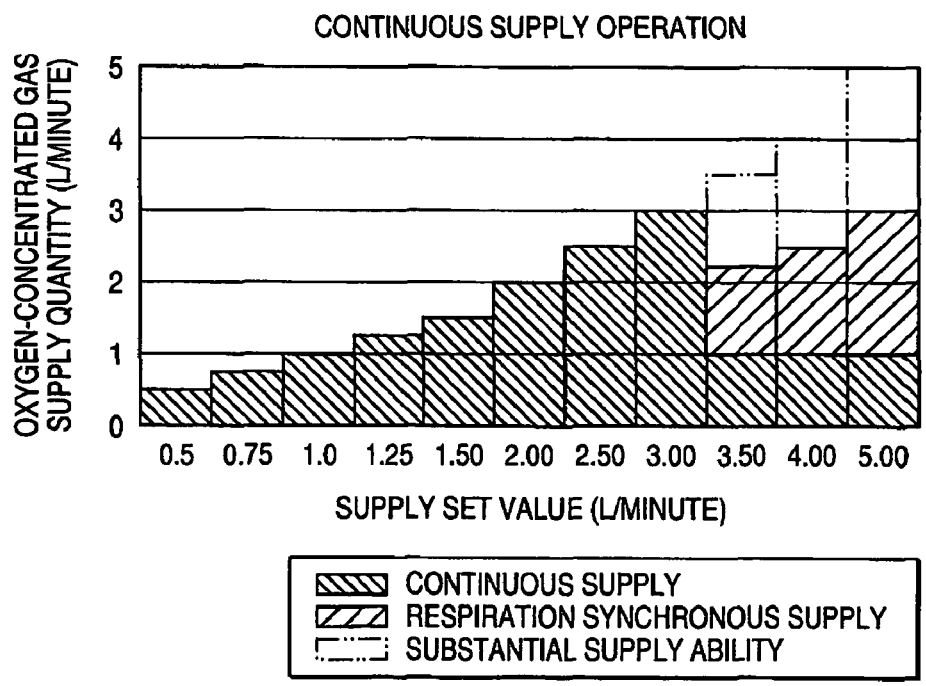
FIG. 8B is a graph showing the relationship between the set supply rate and the oxygen-concentrated gas supply per minute in a case where continuous supply operation has been selected.

In the model having a steady flow, the output (L/minute) of the compressor 1 at the respiration synchronous time was controlled such that ((supply setting−steady flow)/2+steady flow) was made the standard. The graph of FIG. 8A shows the relationship between the supply rate setting and the oxygen-concentrated gas supply per minute in the case where respiration synchronous operation is selected, and the graph of FIG. 8B the relationship between the supply rate setting and the oxygen-concentrated gas supply per minute in the case where continuous supply operation is selected. In these graphs, the compressor 1 carries out an operation with an output generating the quantity of respiration synchronous supply shown by the slanted lines, the electric power consumption is reduced and, if converted in terms of oxygen generating quantity, the portion surrounded by alternate long and short dash lines indicates the energy savings.

Further, in the model having no steady flow, the output (L/minute) of the compressor 1 was controlled with (supply setting/2) being made the standard.

Comparative experiments of electric power consumption were performed by operating the above three types of oxygen concentrating apparatus. As a result, in comparison with the conventional type oxygen concentrating apparatus, the electric power consumption was remarkably reduced as follows:

(1) in the case where the supply setting=1.0 L/minute, electric power consumption was reduced by about 8% in the model having a steady flow, and about 33% in the model having no steady flow, (2) in the case where the supply setting=2.0 L/minute, electric power consumption was reduced by about 8% in the model having a steady flow, and about 32% in the model having no steady flow, and (3) in the case where the supply setting=3.0 L/minute, electric power consumption was reduced by about 23% in the type having a steady flow, and about 37% in the model having no steady flow.

In the conventional type oxygen concentrating apparatus, since a supply of the oxygen exceeding 3.0 L/minute is functionally impossible, a comparison exceeding this value cannot be performed. However, when the comparison of the supply setting=5.0 L/minute was performed with respect to the examples of the present invention, the electric power consumption of the model having no steady flow was lower by about 4% than that of the model having a steady flow.

While the invention has been described in detail and with reference to specific embodiments thereof, it will be apparent to one skilled in the art that various changes and modifications can be made therein without departing from the spirit and scope thereof.

This application is based on Japanese Patent Application Nos. 2003-366769 filed Oct. 28, 2003 and 2004-311045 filed Oct. 26, 2004, the above-noted applications incorporated herein by reference.

What is claimed is:

1. An oxygen concentrating apparatus comprising:
an output variable compressor taking in and supplying compressed air,
a concentration means for increasing oxygen concentration of air supplied by the compressor to thereby produce an oxygen-concentrated gas,
a gas tank for storing the oxygen-concentrated gas produced by the concentration means,
a gas outlet for supplying oxygen-concentrated gas stored in the gas tank to an inhaling person,
a respiration detection means for distinguishing a respiration stage of the inhaling person,
a continuous supply control means for continuously discharging oxygen-concentrated gas from the gas outlet,
a synchronous supply control means for supplying oxygen-concentrated gas to the gas outlet, said supply being synchronized with inhalation or timing of inhalations of the inhaling person, and for storing oxygen-concentrated gas in the gas tank when it is not being supplied to the inhaling person, and
a continuous/synchronous change-over means for allowing a user to select one of the continuous supply control means and the synchronous supply control means,
wherein when synchronous operation is selected, the compressor is operated at a lower output in comparison with continuous operation in the case where the oxygen-concentrated gas supply quantity of the two operations is at the same level.

2. The oxygen concentrating apparatus as claimed in claim 1, wherein said respiration detection means distinguishes the respiration stage of the inhaling person by passage of gas through the gas outlet.

3. The oxygen concentrating apparatus as claimed in claim 1, wherein when synchronous operation is selected, said synchronous supply control means reducing the supply quantity of the oxygen-concentrated gas to the gas outlet at times other than when oxygen-concentrated gas is being synchronously supplied to the inhaling person.

4. The oxygen concentrating apparatus as claimed in claim 1, wherein when synchronous operation is selected, said synchronous supply control means setting the supply quantity of oxygen-concentrated gas to zero at times other than when oxygen-concentrated gas is being synchronously supplied to the inhaling person.

5. An oxygen concentrating apparatus comprising:
an output variable compressor taking in and supplying compressed air,
a concentration means for increasing oxygen concentration of air supplied by the compressor to thereby produce an oxygen-concentrated gas,
a gas tank for storing the oxygen-concentrated gas produced by the concentration means,
a gas outlet for supplying oxygen-concentrated gas stored in the gas tank to an inhaling person,
a respiration detection means for distinguishing a respiration stage of the inhaling person,
a continuous supply control means for continuously discharging oxygen-concentrated gas from the gas outlet,
a synchronous supply control means for supplying oxygen-concentrated gas to the gas outlet, said supply being synchronized with inhalation or timing of inhalations of the inhaling person, and for storing oxygen-concentrated gas in the gas tank when it is not being supplied to the inhaling person, and
a continuous/synchronous change-over means for allowing a user to select one of the continuous supply control means and the synchronous supply control means,
said oxygen concentrating apparatus comprising means for decreasing the compressor output to a level lower than its continuous output supply capacity when synchronous operation is selected.

6. The oxygen concentrating apparatus as claimed in claim 5, wherein said respiration detection means distinguishes the respiration stage of the inhaling person by passage of gas through the gas outlet.

7. The oxygen concentrating apparatus as claimed in claim 5, wherein when synchronous operation is selected, said synchronous supply control means reducing the supply quantity of the oxygen-concentrated gas to the gas outlet at times other than when oxygen-concentrated gas is being synchronously supplied to the inhaling person.

8. The oxygen concentrating apparatus as claimed in claim 5, wherein when synchronous operation is selected, said synchronous supply control means setting the supply quantity of oxygen-concentrated gas to zero at times other than when oxygen-concentrated gas is being synchronously supplied to the inhaling person.

9. An oxygen concentrating apparatus comprising:
an output variable compressor taking in and supplying compressed air,
a concentration means for increasing oxygen concentration of air supplied by the compressor to thereby produce an oxygen-concentrated gas,
a gas tank for storing the oxygen-concentrated gas produced by the concentration means,
a gas outlet for supplying oxygen-concentrated gas stored in the gas tank to an inhaling person,
a respiration detection means for distinguishing a respiration stage of the inhaling person,
a continuous supply control means for continuously discharging oxygen-concentrated gas from the gas outlet,
a synchronous supply control means for supplying oxygen-concentrated gas to the gas outlet, said supply being synchronized with inhalation or timing of inhalations of the inhaling person, and for storing oxygen-concentrated gas in the gas tank when it is not being supplied to the inhaling person, and
a continuous/synchronous change-over means for allowing a user to select one of the continuous supply control means and the synchronous supply control means wherein said synchronous supply control means comprises means for continuously supplying a steady state flow of oxygen-concentrated gas in addition to said synchronized supply, said oxygen concentrating apparatus comprising means for decreasing the compressor output to about ½ its continuous output supply capacity when synchronous operation is selected and a steady state flow of oxygen-concentrated gas is supplied in addition to said synchronized supply.

10. The oxygen concentrating apparatus as claimed in claim 9, wherein said respiration detection means distinguishes the respiration stage of the inhaling person by passage of gas through the gas outlet.

11. The oxygen concentrating apparatus as claimed in claim 9, wherein when synchronous operation is selected, said synchronous supply control means reducing the supply quantity of the oxygen-concentrated gas to the gas outlet at times other than when oxygen-concentrated gas is being synchronously supplied to the inhaling person.

12. The oxygen concentrating apparatus as claimed in claim 9, wherein when synchronous operation is selected, said synchronous supply control means setting the supply quantity of oxygen-concentrated gas to zero at times other than when oxygen-concentrated gas is being synchronously supplied to the inhaling person.

13. An oxygen concentrating apparatus comprising:
an output variable compressor taking in and supplying compressed air,
a concentration means for increasing oxygen concentration of air supplied by the compressor to thereby produce an oxygen-concentrated gas,
a gas tank for storing the oxygen-concentrated gas produced by the concentration means,
a gas outlet for supplying oxygen-concentrated gas stored in the gas tank to an inhaling person,
a respiration detection means for distinguishing a respiration stage of the inhaling person,
a continuous supply control means for continuously discharging oxygen-concentrated gas from the gas outlet,
a synchronous supply control means for supplying oxygen-concentrated gas to the gas outlet, said supply being synchronized with inhalation or timing of inhalations of the inhaling person, and for storing oxygen-concentrated gas in the gas tank when it is not being supplied to the inhaling person, and
a continuous/synchronous change-over means for allowing a user to select one of the continuous supply control means and the synchronous supply control means,
wherein said respiration detection means distinguishes inhalation and exhalation of the inhaling person, and said synchronous supply control means comprises means for setting the supply quantity of oxygen-concentrated gas to zero during exhalation,
said oxygen concentration apparatus comprising means for decreasing the compressor output to about ⅓ its continuous output supply capacity when synchronous supply control is selected and the supply quantity of oxygen-concentrated gas is set to zero during exhalation.

14. The oxygen concentrating apparatus as claimed in claim 13, wherein said respiration detection means distinguishes the respiration stage of the inhaling person by passage of gas through the gas outlet.

15. The oxygen concentrating apparatus as claimed in claim 13, wherein when synchronous operation is selected, said synchronous supply control means reducing the supply quantity of the oxygen-concentrated gas to the gas outlet at times other than when oxygen-concentrated gas is being synchronously supplied to the inhaling person.

16. The oxygen concentrating apparatus as claimed in claim 13, wherein when synchronous operation is selected, said synchronous supply control means setting the supply quantity of oxygen-concentrated gas to zero at times other than when oxygen-concentrated gas is being synchronously supplied to the inhaling person.

* * * * *